United States Patent
Von Gutfeld et al.

(10) Patent No.: US 6,337,627 B1
(45) Date of Patent: Jan. 8, 2002

(54) SYSTEM OF PROVIDING MEDICAL TREATMENT

(75) Inventors: Robert J. Von Gutfeld, New York, NY (US); James F. Ziegler, Edgewater, MD (US); Scott J. McAllister, Poughkeepsie, NY (US); James H. Anderson, Columbia, MD (US); John C. Murphy, Clarksville, MD (US); Matthias D. Ziegler, Edgewater, MD (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/699,183

(22) Filed: Oct. 27, 2000

(51) Int. Cl.$^7$ ................................................ G08B 13/14
(52) U.S. Cl. ............................... 340/572.1; 340/572.2; 340/551; 340/572.4; 340/540; 424/111; 424/9.1; 324/326; 324/207.12
(58) Field of Search ........................... 340/572.1, 572.2, 340/551, 572.4, 540; 424/111, 9.1; 324/326, 207.12

(56) References Cited

U.S. PATENT DOCUMENTS

| | | | | |
|---|---|---|---|---|
| 5,051,034 A | * | 9/1991 | Goodman | 405/157 |
| 5,423,334 A | * | 6/1995 | Jordan | 128/899 |
| 5,532,598 A | * | 7/1996 | Clark, Jr. et al. | 324/326 |
| 5,538,803 A | * | 7/1996 | Gambino et al. | 428/694 TM |
| 5,729,129 A | * | 3/1998 | Acker | 324/207.12 |
| 5,833,603 A | * | 11/1998 | Kovacs et al. | 600/317 |
| 5,846,513 A | * | 12/1998 | Carroll et al. | 424/111 |

* cited by examiner

Primary Examiner—Daniel J. Wu
Assistant Examiner—Tai T. Nguyen
(74) Attorney, Agent, or Firm—Lauren C. Bruzzone

(57) ABSTRACT

The invention describes methods for locating a treatment device disposed within a living body by means of magnetic fields that are produced by Barkhausen jumps, principally from amorphous tag wires with high permeability that exhibit reentrant flux reversal. When wires of this type are attached to concealed treatment devices such as catheters, interrogation or scanning of the tag wire by a low frequency ac magnetic field affords an accurate means for locating the treatment devices using a sensor coil to detect the magnetic field signal from the wire locating tag. The strength of the field detected by the position of a sensor coil with respect to the locator tag is used to determine the location of the tag. A favorable signal to noise detection ration is obtained as the signal emitted by the wire is at a very high frequency compared to that of the frequency of the interrogation field.

12 Claims, 3 Drawing Sheets

H = CONSTANT

SYSTEM OF PROVIDING MEDICAL TREATMENT

FIELD OF THE INVENTION

The present invention relates to the use of magnetic tag elements to locate concealed inanimate objects to which such tags are attached. Such inanimate objects should be understood to include movable objects, such as surgical instruments and other medical treatment devices which must be positioned and controlled within a living body during medical treatment, as well as fixed objects which may need to be located, such as buried sewer pipes and fiber-optic cables. The invention also relates to the provision of medical treatments with treatment devices which are concealed within a living body.

The invention relates to a system of tagging, as well as the means and method for finding, locating and/or tracking preferably nonmagnetic objects. Examples of the application include: tracking of medical diagnostic, surgical or therapeutic tools used on or within a human or animal body, determining the location of hidden objects such as landmines, buried fiber-optic cables or plastic plumbing pipes, determining the position of an object subjected to computer or automated control, locating errant golf-balls.

BACKGROUND OF THE INVENTION

There are numerous instances where it is important to locate an object out of visual contact or where monitoring the movement of an invasive object such as a catheter is required in order to know for example, where the tip of the catheter is located. While much of this can be done using MRI or x-ray techniques, the equipment and its use for such monitoring is expensive and somewhat cumbersome. Furthermore, the extensive use of x-rays for monitoring objects within humans is to be avoided whenever possible for health reasons. It therefore becomes preferable to be able to monitor such hidden objects by methods that are easy to utilize and which at the same time give a very accurate position of the object. In addition, a large signal to noise ratio is desirable.

SUMMARY OF THE INVENTION

Broadly, the present invention provides a system for determining the location of an inanimate object after attachment, to the object, of an element (or "tag") comprising a magnetic material, the aforesaid system comprising:

a) an aforesaid element which is capable of emitting a non-linear magnetic signal in response to an applied ac magnetic field, b) a magnetic field generator for irradiating the aforesaid element with an applied ac magnetic field, c) a movable magnetic field sensor operable to detect the aforesaid non-linear magnetic signal from a plurality of selected mutually displaced positions to produce a corresponding plurality of element-locating signals, and d) a computing apparatus for converting the aforesaid element-locating signals to a location image of the aforesaid object.

The invention also provides a method for determining the location of a concealed inanimate object, the method comprising the steps of:

a) attaching, to this object, an element comprising a magnetic material which is capable of emitting a non-linear magnetic signal in response to an applied ac magnetic field, b) irradiating the aforesaid element with an applied ac magnetic field, c) moving a magnetic field sensor in spaced adjacency to the aforesaid element to detect the aforesaid non-linear magnetic signal from a plurality of selected mutually displaced positions to represent a corresponding plurality of element-locating signals, and d) converting the aforesaid element-locating signals to a location image of the aforesaid object.

Preferably, the aforesaid element comprises an amorphous magnetic material capable of emitting a non-linear magnetic signal which is characterized by Barkhausen jumps in response to the aforesaid applied ac magnetic field. Moreover, it is preferred that the aforesaid element (or "tag") comprises an amorphous magnetic wire characterized by a magnetization which is reversible in direction in response to the aforesaid applied ac field, the magnitude of which may be selected as a function of the length or other dimension of the amorphous magnetic wire.

As will be understood, the aforesaid inanimate object, which is to be located, should preferably be non-magnetic and may take many different forms. For example, the object may be a medical treatment device such as a catheter, surgical instrument, brachytherapy tube, or therapeutic radiation device that is disposed within a living body, whether such object has merely been misplaced or needs to be controlled and manipulated while in its concealed position. Alternatively, the object may be a hidden underground sewer pipe, optical fiber cable, or even a valuable instrument that may be inadvertently buried during excavation. Other applications will be readily identifiable as well.

The invention also provides a system for providing medical treatment to a living body with a treatment device, the system comprising:

a) a treatment device disposed within said living body, b) an element or "tag" (as described herein above) attached to the aforesaid treatment device, wherein this element comprises a magnetic material and is capable of emitting a non-linear magnetic signal in response to an applied ac magnetic field, c) a magnetic field generator for irradiating the aforesaid element and a juxtaposed region of the living body with an applied ac magnetic field, d) a movable magnetic field sensor operable to detect the aforesaid non-linear magnetic signal from a plurality of selected mutually displaced positions to produce a corresponding plurality of element-locating signals, e) a computing apparatus for converting the aforesaid element-locating signals to a location image of the treatment device, and f) a controller device for controlling the position and treatment action of the treatment device in synchronism with the aforesaid location image.

Preferably, the treatment device may be a catheter, surgical instrument, brachytherapy tube holding one or more radioactive particles, a therapeutic radiation emitting device, or the like.

The invention also provides a method for providing medical treatment to a living body with a treatment device concealed therein, comprising the steps of:

a) attaching, to the treatment device, an element (as described herein above) comprising a magnetic material, the aforesaid magnetic material being capable of emitting a non-linear magnetic signal in response to an applied ac magnetic field, b) irradiating the aforesaid element with an applied ac magnetic field, c) moving a magnetic field sensor in spaced adjacency to the aforesaid element to detect the aforesaid non-linear magnetic signal from a plurality of selected mutually displaced positions to represent a corresponding plurality of element-locating signals, d) converting the aforesaid element-locating signals to a location image of the aforesaid treatment device, and e) controlling the position and treatment action of the aforesaid treatment device in synchronism with the aforesaid location image.

The novelty of the present invention utilizes a sharp Barkhausen jump or sudden change in magnetization of an amorphous magnetic material attached to an object, the magnetic material acting as a locator or tag. A relatively high frequency magnetic signal compared to the frequency of an interrogating magnetic field is emitted by the magnetic element or tag. The wire which is utilized in the preferred embodiment has been developed by Unitika, Ltd., Kyoto, Japan. The wire is formed by a technique that uses a molten metal sprayed onto a cold water surface on a rotating wheel, a process referred to an "in-rotating-water-quenched." This spin melting and rapid quenching results in an amorphous rather crystalline state of the resulting magnetic alloy. The magnetic signal resulting from the flux reversal in such a wire can be readily discriminated from the excitation signal because the wires' emitted magnetic frequency spectrum contains components that are several orders of magnitude higher than that of the excitation signal.

The use of such a wire as an implant onto a tumor to locate the position of the tumor during periods of radiation treatment is disclosed in co-pending U.S. patent application Ser. No. 09/241,506, entitled, "IMAGING OF INTERNAL STRUCTURES OF LIVING BODIES BY SENSING IMPLANTED MAGNETIC DEVICES," filed Feb. 1, 1999, by von Gutfeld, et al.

The "locating apparatus" is comprised of two parts. The first component is a magnetic field generator or excitation coil which emits a low frequency ac magnetic field of intensity greater than ~0.5–1 Oersteds in the region of the position of the locator tag, along the direction of the wire or foil. The second component consists of one or more movable magnetic field sensors or sensing coils to detect the emitted Barkhausen jumps or sudden changes in magnetic field arising from the locator tag under the influence of the field of the excitation coil.

The apparatus and method of search can be used in a variety of medical applications such as the tracking of a catheter within the body of a human or animal. More generically, one or more short lengths of wires can be attached along the lengths of plastic pipes or fiber optic cables to be buried and later located, or even attached to explosives such as land-mines, or golf balls, to enable their positions to be determined at a future time.

BRIEF DESCRIPTION OF THE DRAWINGS

FIG. 1d shows a hypodermic device capable of injecting a tag as shown in FIG. 1a.

DETAILED DESCRIPTION OF THE INVENTION

Figure 1A:
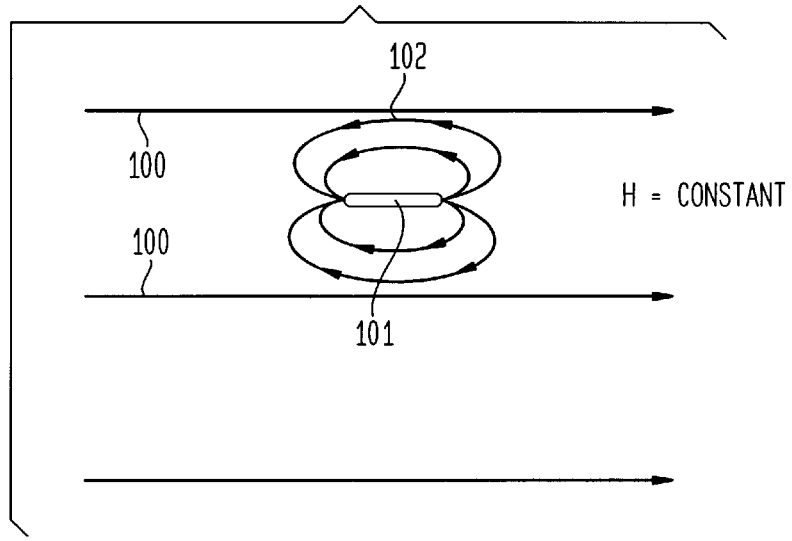
FIG. 1a is a schematic view of an element or locator tag in accordance with this invention.

In the present invention a tag element such as a remotely located amorphous, highly permeable wire, is interrogated with a small magnetic ac excitation field. Typically, the tag element could be 10–200 microns in diameter and 1–10 cm in length. When limited to small ac fields, on the order of 0.5–1.0 Oersteds in absolute value in a direction parallel to the axis of the wire, the flux along the axis of the wire undergoes a sharp reversal in direction known as reentrant flux reversal with every half cycle of the excitation sine wave (other shapes of waves can also be used so long as they have a positive and negative periodicity). The value of excitation field, typically on the order of 0.5–1.0 Oersteds, at which this sharp reversal occurs is generally referred to as H* in the technical literature with H* in a direction that is opposite to that of the wire's direction of magnetization. This change in the excitation field results in a sudden emission of magnetic flux emanating from the wire which can be detected by a pickup coil and easily discriminated from the ac excitation field through appropriate filters. The frequency of the excitation field can, though need not be limited to the range 10–1000 Hz. This sudden change, which is not only abrupt but also involves a change in sign (180 degree reversal) in the wire's core magnetization due to the wire's change in reentrant flux reversal is an example of a large "Barkhausen jump". The use of small amplitude excitation magnetic fields to irradiate a tag element is one mode of operation which is desirable, especially in the presence of living organisms. However a much larger ac excitation field can also be used which results in a flux reversal of the wire but is not the preferred embodiment. When larger excitation fields are used, that is larger than H*, the reentrant flux reversal will not be as sharp or sudden. Hence there will be fewer high frequency components in the emitted signal. Details of these reentrant effects as a function of the strength of the excitation field are described by Soeda, et al, in IEEE Transactions on Magnetics, Volume 31, 3877 (1995) but are not immediately relevant to the present invention.

In the preferred mode of operation of our invention, the amorphous wire or locator tag reverses its direction of magnetization in a Barkhausen jump at a fixed requisite value of magnetic excitation field the value of which is influenced by the dimensions of said wire. Additional discussion of the hysteresis curves resulting from varying field conditions applied to the amorphous wires are described by Humphrey in U.S. Pat. No. 4,660,025.

According to the invention, the magnitude of the field emitted from the wire is measured by a movable magnetic field sensor coil, and is a function of position of the magnetic field sensor coil with respect to the position of the locator tag. The sensor coil measures the rate of change of magnetic flux with respect to time, well known to those skilled in the art with the magnetic field of interest emanating from the locator tag due to the excitation field. The change in flux with time results in an element-locating signal in the form of a voltage induced in the sensor coil, as is well known to those skilled in the art.

The magnitude of the field emitted by the wire as a function of the position of a magnetic field sensor coil determines the location of the locator tag or wire. Since the amorphous wire emits a dipole field, it is relatively simple to precisely locate either end of the wire, or its midpoint, which determines the location being sought in two dimensions. Additional sensor coil readings are required to determine a three dimensional location which in many applications is not necessary.

Details of the invention can best be described by referring to the figures. FIG. 1a shows an amorphous magnetic wire 101, which exhibits the reentrant flux reversal phenomenon. The wire is made by a rotating wheel melt-quench process. Wire 101 typically comprises an alloy of Fe—Si—B or Fe—Co—Si—B. In the presence of a static magnetic field 100 the wire has magnetic core, that is interior, and surface domains. A 180 degree reversal in direction of the core domains or magnetization directed along the length of the wire 101, occurs when the applied ac interrogating field reverses polarity with respect to the magnetization, hence there are two opposite directions for the magnetization of the wire. The magnetic flux reversal occurs when the direction of the applied magnetic field 100 reverses direction and reaches a value of field at wire 101 on the order of 0.5–1 Oersteds, a value of field also known as H*. For a given direction of the applied magnetic field 100 as shown in FIG. 1a, the induced field of wire 101 is a dipole with magnetic field lines 102. In order to use the wire as a locator element or "tag", the wire 101 is attached to an object to be located at a later time. When attached to an object, wire 101 is referred to as a locator tag 101. The field strength emitted by wire 101 in the presence of the applied source of an ac magnetic interrogating field 100 is measured with a magnetic field sensor coil (flux gates, Hall probes, SQUIDS, etc., could also be used as is well known to those skilled in the art of magnetic field measurements) as a function of the sensor coil position relative to the locator tag.

Figure 1B:
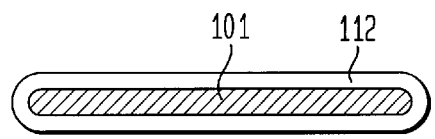
FIG. 1b shows a segment of wire in accordance with this invention.

FIG. 1b shows the magnetic wire 101 encapsulated in a non- magnetic encapsulant 112 to protect the wire from moisture or other possible contaminants damaging to wire 101.

Figure 1C:
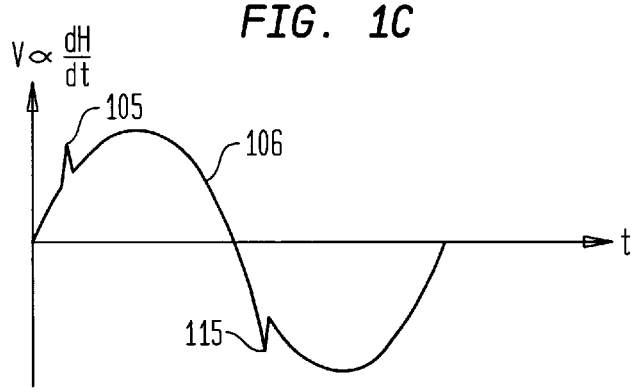
FIG. 1c shows the voltage detected upon irradiation of the wire shown in FIG. 1b with an ac magnetic field.

The magnetic behavior of wire 101 when interrogated by a magnetic field generator as a source of an ac magnetic field 100 is shown in FIG. 1c. In the presence of an ac magnetic field H, the voltage detected by a sensor coil is directly proportional to the rate of change of magnetic field, dH/dt, with respect to time. The sensor coil will therefore detect both a component of the applied time varying field (e.g. 60 Hz) and the change in field as a function of time or Barkhausen jump of wire 101 due to the reentrant flux reversal. This relationship is shown graphically in terms of the sensor voltage dH/dt 106 as a function of t in FIG. 1c. The curve of dH/dt, 106, with time t due to the detected total field as sensed by a magnetic field sensor coil (sensor coil 303 in FIG. 3a) consists of a sinusoidal voltage 106 and a superposition of smaller magnetic high frequency voltage spikes 105 and 115 occurring in opposite directions as a function of time. The voltage spike 105 occurs when the reentrant flux reversal of wire 101 takes place. The reentrant flux reversing direction from its given direction along wire 101 while spike 115 occurs when the sinusoidal field 100 again reverses direction resulting in a second Barkhausen jump with emitted flux in the opposite sense. The values of the interrogating field at which these spikes occur are designated in the technical literature (e.g. the aforementioned article by Soeda et al) as H*. For tag wires 101, H* is generally on the order of 0.5–1 Oersted. The magnetic field spikes 105 and 115 and their respective relative amplitudes are the means for determining the location of wire 101.

Figure 1D:
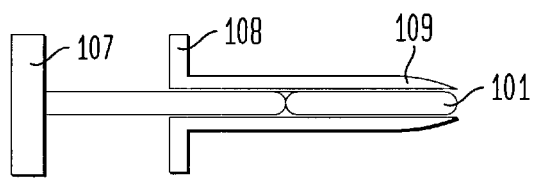

Wire 101 with or without encapsulant 112 (FIG. 1b) can be inserted into or attached to an object by way of a hypodermic type device shown in FIG. 1d. The plunger 107 fits into a holder 108 which can inject wire 101 through a needle 109 into an object by pushing on plunger 107. Alternatively, element 101 may be affixed to an inanimate, concealed object by a clamp, adhesive or other means prior to the object (e.g. catheter or other treatment device) becomes concealed.

Figure 2:
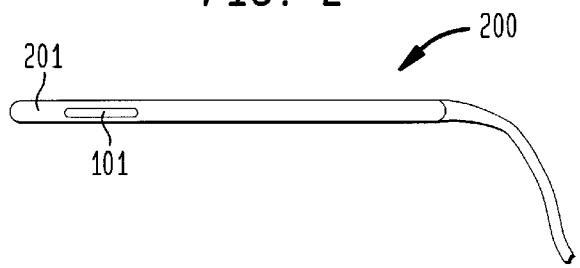
FIG. 2 shows the tag of FIG. 1a attached to a catheter which can be inserted into an animal or human for diagnostic or treatment purposes.

FIG. 2 shows an object in the form of a catheter 200 typically used for medical diagnostic or treatment purposes with wire 101 attached to the inner surface 201 of catheter 200. Here wire 101 after attachment to 201 acts as a locator tag.

Figure 3A:
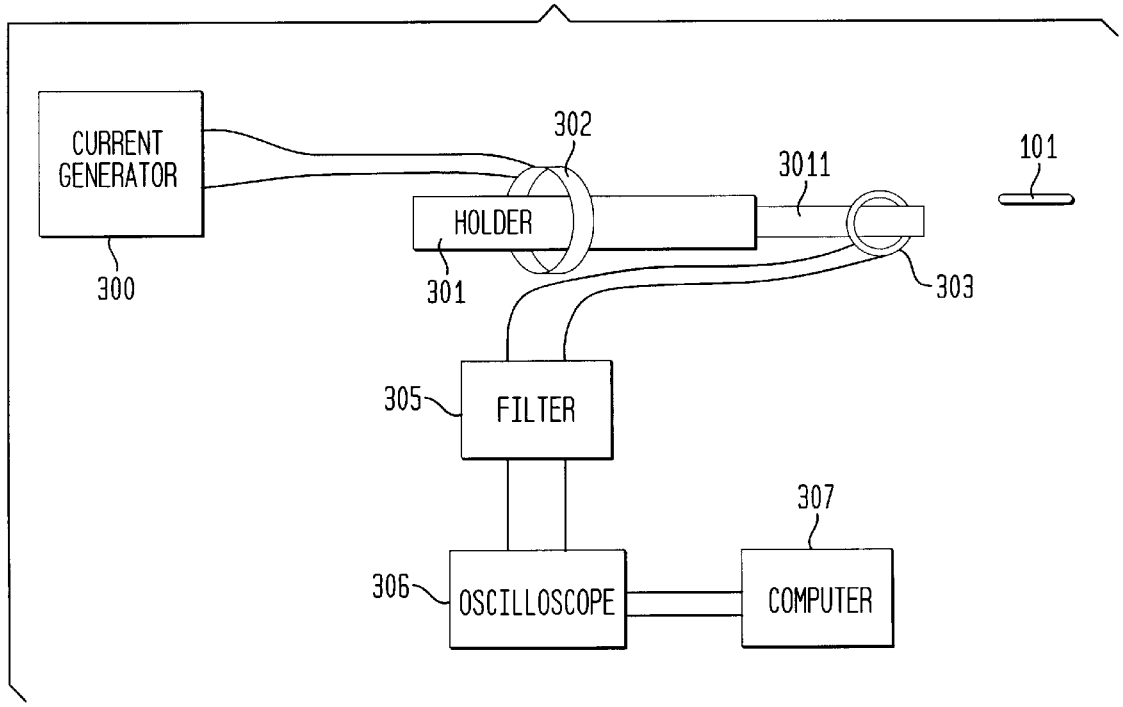
FIG. 3a shows a system in accordance with invention where in the magnetic field of the magnetic field generator is joined to the movable mean field sensor.
Figure 3B:
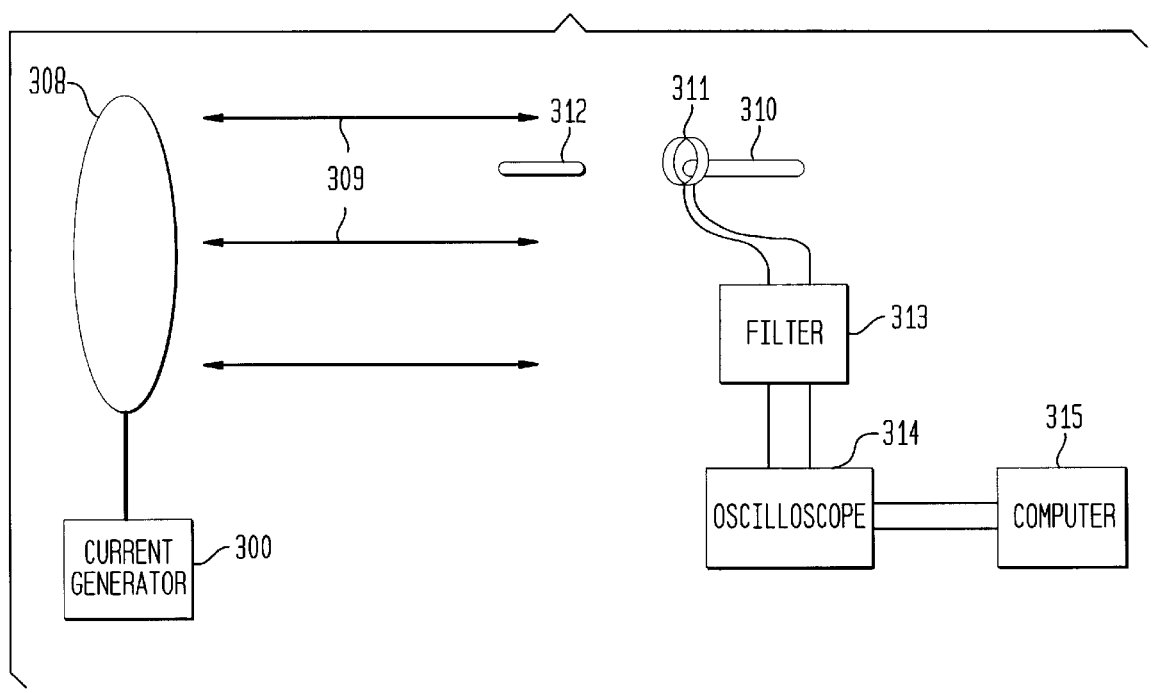
FIG. 3b shows the system of FIG. 3a where the field coil is stationary.

FIGS. 3a and 3b show schematics with appropriate components for applying the excitation field 100 (and 309 in FIG. 3b) and sensing of the fields 105 and 115 from tag element or wire 101 as a function of distance between the sensing or pickup coil and the tag wire. FIG. 3a shows an ac current generator 300 which sends curt through field coil 302 wrapped about a portable holder 301. The current generates the ac magnetic excitation field 100 and the resulting sensor voltage 106 shown in FIG. 1c to irradiate and excite the magnetic wire 101. A movable magnetic field sensor coil 303 mounted on the support section 3011 detects both the magnetic excitation field 309 and the time dependent reentrant magnetic field 105 and 115 from wire 101 with respect to position of the attached wire 101, the locator tag.

To separate the voltage induced in sensor coil 303 by the sinusoidal magnetic field and field spikes 105 and 115 a filter 305 is used, designed to pass only the high frequencies of spikes 105 and 115. As holder 301 is moved in relation to wire 101, an oscilloscope 306 can be used to determine the magnitude of voltage spikes 105 and 115. The values of these two magnitudes of element-locating signals can also be stored and compared to stored field patterns in the memory of computer 307, hereby to form a location image of wire 101 and the object to which it is attached.

Figure 3C:
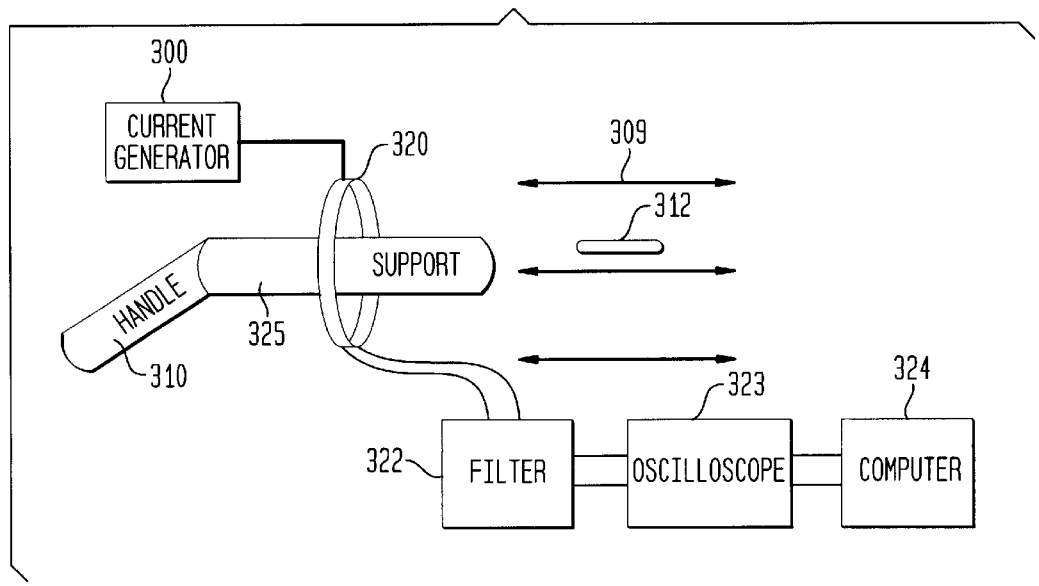
FIG. 3c shows the system of FIG. 3a where a single coil is used as both field coil and as magnetic sensor.

Similarly, FIG. 3b shows coil 308 attached to the current generator 300 to provide an ac interrogation field 309, here shown schematically but shown in detail in FIG. 1c. A sensing coil 311 is mounted on a portable handle 310 to sense the field from wire 312. Again the field from coil 308 will also be sensed so that filter 313 is used to separate field-induced voltages 106 and 105, leaving only 105 to be detected by oscilloscope 314 and directed to computer 315 for signal comparison, storage and conversion into a location image of the tag element 312. FIG. 3c shows details of an alternative structure for both exciting and sensing the magnetic fields. Coil 320, wrapped on support 325 is attached to current generator 300 while also attached to filter 322 which separates the excitation field 309 from the field from tag wire 312. An oscilloscope 323 is used to display the voltages proportional to the magnetic fields from filter 322 as a function of position using the handle 310 for moving the device into the desired positions.

The element-locating signals are then converted to a location image of the tag element (wire 312) by computer 324.

Figure 4:
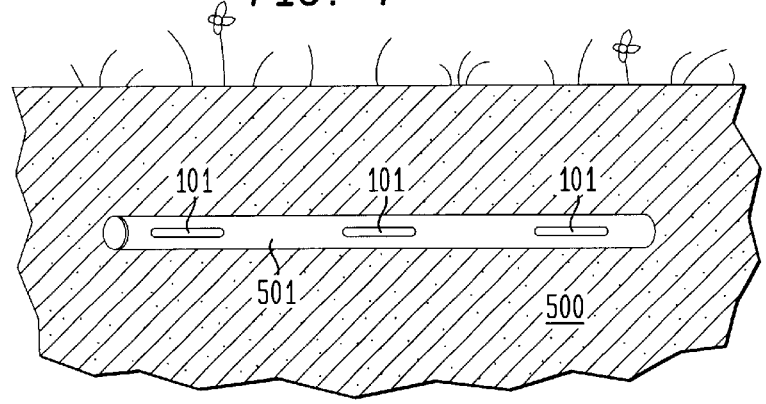
FIG. 4 shows a tag in the form of an amorphous magnetic wire attached to a plastic pipe or optic fiber cable buried under ground.

FIG. 4 shows the attachment of tag wires 101 to sections of a nonferrous object, such as a pipe 501 buried under ground 500. To locate pipe 501, an ac magnetic excitation field 309 can be applied using the scheme outlined in FIG. 3a, 3b, and 3c again sensing the values of the voltage spikes 105 and 115 of the field induced in a sensing coil 303, 311 or 320 as a function of position with respect to wires 101. It should be clear to those skilled in the art that the concept of attaching the amorphous magnetic wires is applicable to a variety of other hidden articles that need to be located in real time or at some later date. For example, a short section of wire can be implanted within objects such as golf balls which may get hidden in underbrush or elsewhere on a golf range.

These objects, whose location is to be determined, require attachment of a "locator tag" consisting of one or more sections of amorphous, highly permeable wire, typically 10–200 $\mu$m in diameter, ~1.0 to 10 cm in length The wire exhibits a sharp "Barkhausen jump", that is an abrupt or nearly discontinuous change in the magnitude of the magnetization due to a very small change in applied magnetic field. In the technical literature, the applied magnetic field required to bring about this change in magnetization is generally referred to as H*, on the order of 0.5–1.0 Oersteds. The change in magnetization is not only abrupt but also reverses sign as a result of a phenomenon known as reentrant flux reversal.

While the use of amorphous magnetic wire is considered to be the preferred embodiment for the present invention, there are other materials that could be used. One such example is amorphous highly permeable magnetic foils that also exhibit very sharp changes in magnetization with small changes in applied magnetic field. This sharp change in magnetization is due to the very narrow and nonlinear hysteresis curves of such foils. Such materials generally come in the form of thin ribbons (25–50 microns in thickness, at one time sold by Allied Signal under the trade name Metglas™). These materials are also usable as magnetic markers for the present invention; however, bulkier and less flexible than the preferred amorphous magnetic wires.

It will be well known to those skilled in the art that while the invention has been described in terms of a sinusoidally varying excitation field, other time varying fields can also be used to obtain similar results.

While the present invention has been described with reference to preferred embodiments thereof, numerous obvious changes and variations may readily be made by persons skilled in the field of magnetic devices. Accordingly, the invention should be understood to include all such variations to the full extent embraced by the claims.

What is claimed is:

1. A system for providing medical treatment to a living body with a treatment device, said system comprising:
    a) a said treatment device disposed within said living body,
    b) an element attached to said treatment device, wherein said element comprises a magnetic material and is capable of emitting a non-linear magnetic signal in response to an applied ac magnetic field,
    c) a magnetic field generator for irradiating said element and a juxtaposed region of said living body with an applied ac magnetic field,
    d) a movable magnetic field sensor operable to detect said non-linear magnetic signal from a plurality of selected mutually displaced positions to produce a corresponding plurality of element-locating signals,
    e) a computing apparatus for converting said element-locating signals to a location image of said treatment device, and
    f) a controller device for controlling the position and treatment action of said treatment device in synchronism with said location image.

2. A system as set forth in claim 1, wherein said element comprises an amorphous magnetic material, said non-linear magnetic signal being characterized by Barkhausen jumps in response to said applied ac magnetic field.

3. A system as set forth in claim 2, wherein said treatment device is a catheter.

4. A system as set forth in claim 2, wherein said treatment device is a surgical instrument.

5. A system as set forth in claim 1, wherein said element comprises an amorphous magnetic wire characterized by a magnetization which is reversible in direction in response to said applied ac field.

6. A system as set forth in claim 1, wherein said treatment device is a catheter.

7. A system as set forth in claim 1, wherein said treatment device is a surgical instrument.

8. A method for providing medical treatment to a living body with a treatment device concealed therein, comprising the steps of:
    a) attaching, to said treatment device, an element comprising a magnetic material, said magnetic material being capable of emitting a non-linear magnetic signal in response to an applied ac magnetic field,
    b) irradiating said element with an applied ac magnetic field,
    c) moving a magnetic field sensor in spaced adjacency to said element to detect said non-linear magnetic signal from a plurality of selected mutually displaced positions to represent a corresponding plurality of element-locating signals,
    d) converting said element-locating signals to a location image of said treatment device, and
    e) controlling the position and treatment action of said treatment device in synchronism with said location image.

9. A method as set forth in claim 8, wherein said element comprises an amorphous magnetic material, said non-linear magnetic signal being characterized by Barkhausen jumps in response to said applied ac magnetic field.

10. A method as set forth in claim 9, wherein said treatment device is a catheter.

11. A method as set forth in claim 9, wherein said treatment device is a surgical device.

12. A method as set forth in claim 9, wherein said treatment device is a hollow brachytherapy tube holding at least one radioactive particle.

* * * * *